US00PP23883P3

(12) United States Plant Patent
Goffreda et al.

(10) Patent No.: US PP23,883 P3
(45) Date of Patent: Sep. 10, 2013

(54) PEACH TREE NAMED 'NJ355'

(50) Latin Name: ***Prunus persica* L.**
Varietal Denomination: NJ355

(75) Inventors: Joseph C. Goffreda, Millstone Township, NJ (US); Anna M. Voordeckers, East Windsor Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 6 days.

(21) Appl. No.: 13/200,086

(22) Filed: Sep. 16, 2011

(65) Prior Publication Data

US 2013/0074228 P1 Mar. 21, 2013

(51) Int. Cl.
*A01H 5/00* (2006.01)

(52) U.S. Cl.
USPC ..... Plt./195

(58) Field of Classification Search
USPC ..... Plt./195
See application file for complete search history.

*Primary Examiner* — Kent L Bell
(74) *Attorney, Agent, or Firm* — James A. Lucas; Driggs, Hogg, Daugherty & Del Zoppo Co., LPA

(57) ABSTRACT

A new and distinct peach variety of *Prunus persica* named 'NJ355' is provided. This variety is distinguished from other peach varieties by its unique combination of non-showy flowers, fruit that ripen in early-season with an attractive red and greyed-purple over color and orange-white ground color, clingstone fruit with a juicy, firm nonmelting texture and sweet, slightly acidic flavor, and excellent production of firm fruit that maintain their eating quality following cold storage.

6 Drawing Sheets

Latin name of genus and species of the plant claimed: *Prunus persica* L.

Variety denomination: 'NJ355'.

CROSS REFERENCE TO RELATED APLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of peach tree named 'NJ355'. Our new tree resulted from open pollination of the seed parent, J19-19-862144. The new variety differs from seed parent J19-19-862144 (unpatented) in that fruit of the new variety ripen approximately 3 weeks earlier and the flesh of the fruit clings to the pit when it is fully ripe. In comparison to the commercial peach variety 'Sugar May' (U.S. Plant Pat. No. 8,034), the fruit of the new variety has a lighter red blush, is lower in acidity, and matures approximately 6 days later. The fruit and leaves of the new variety are also more tolerant to bacterial leaf spot than 'Sugar May'. The resulting tree was selected when growing in a cultivated area as the $44^{th}$ tree in the $4^{th}$ row of Block H at a fruit research center in Cream Ridge, N.J.

BRIEF SUMMARY OF THE INVENTION

The 'NJ355' variety is distinguished from other peach varieties due to the following unique combination of characteristics:

Round fruit with a low tendency to split for the season.

Attractive fruit with a red and greyed-purple over color and orange-white ground color.

Excellent production of very firm fruit that ripen in early-season.

Fruit with a good to very good eating quality.

The variety was asexually reproduced at the research center in Cream Ridge, N.J. Asexual reproduction of this new variety by budding onto 'Lovell' rootstock (unpatented) shows that the foregoing characteristics are so reproduced.

The following detailed description concerns the original tree, 'NJ355'. The original tree and asexual progeny have been observed growing in a cultivated area at the research center in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966 Edition).

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
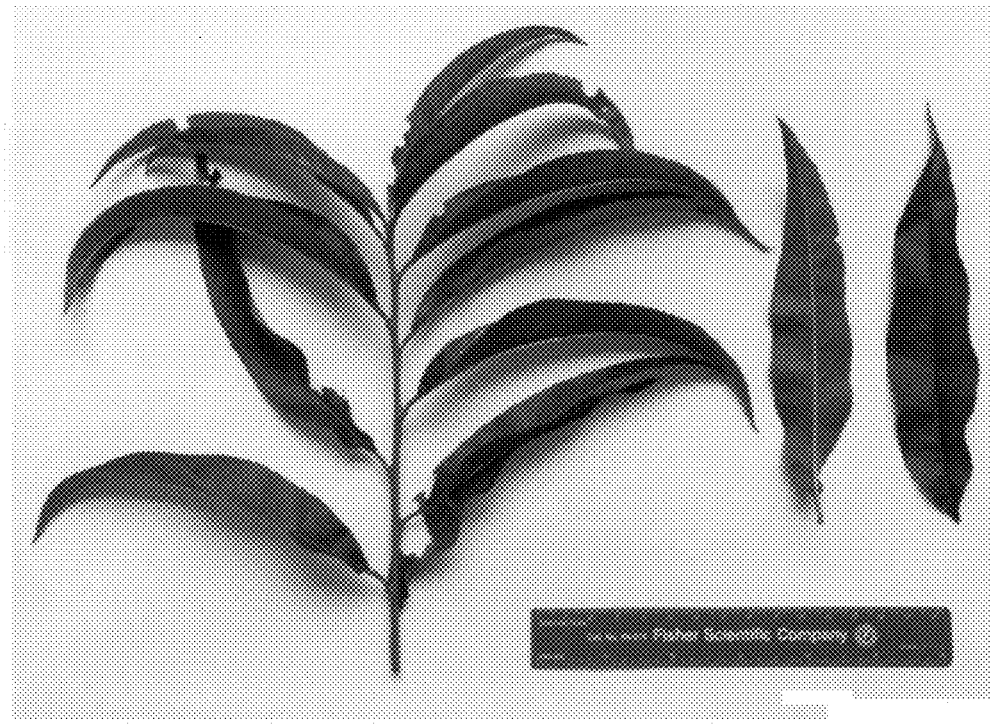
FIG. 1 is a color photograph taken on Jul. 19, 2010 of a characteristic twig of 'NJ355' in late summer bearing typical leaves of the mature foliage.
Figure 2:
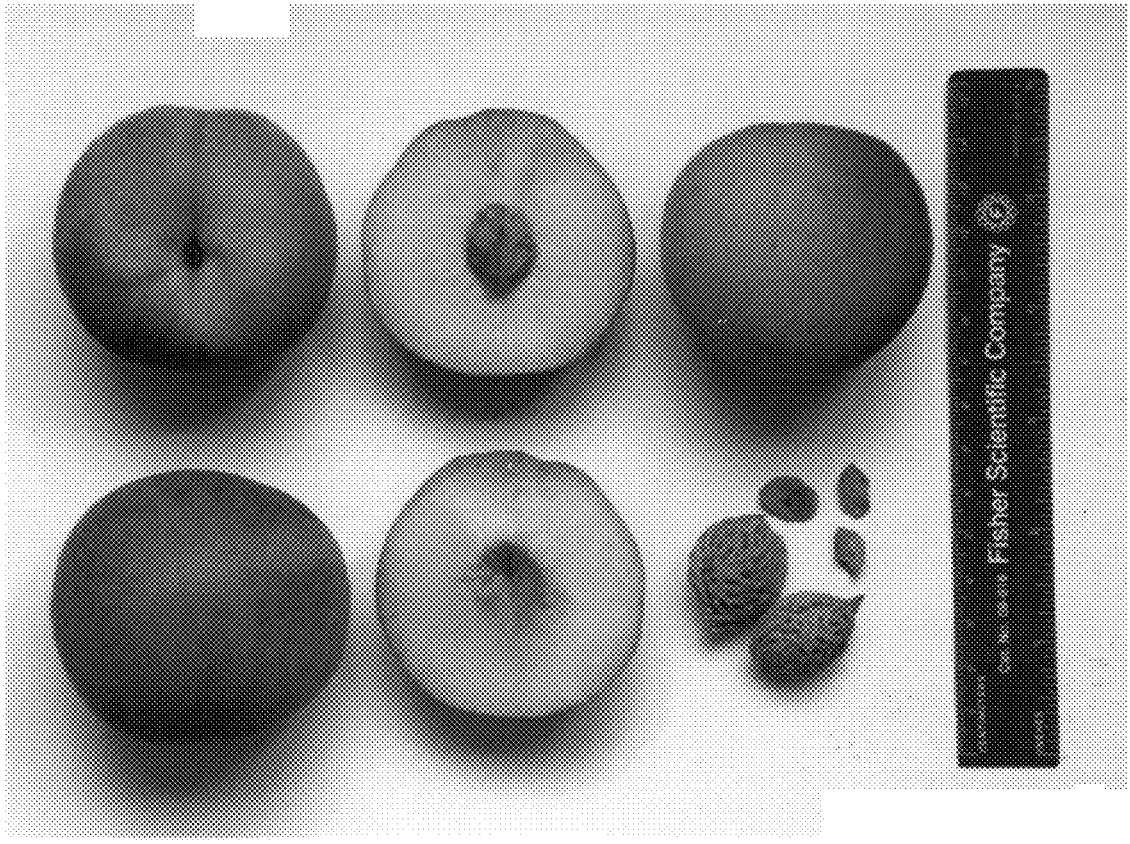
FIG. 2 is a color photograph taken on Jul. 14, 2010 of characteristic mature fruit and stones of 'NJ355'. Whole fruit are presented in three positions and a transverse cross section to show that the pericarp tends to adhere to the pit when the fruit is mature. The stones illustrate the ovoid shape and the pit grooves on the surface of the stone.
Figure 3:
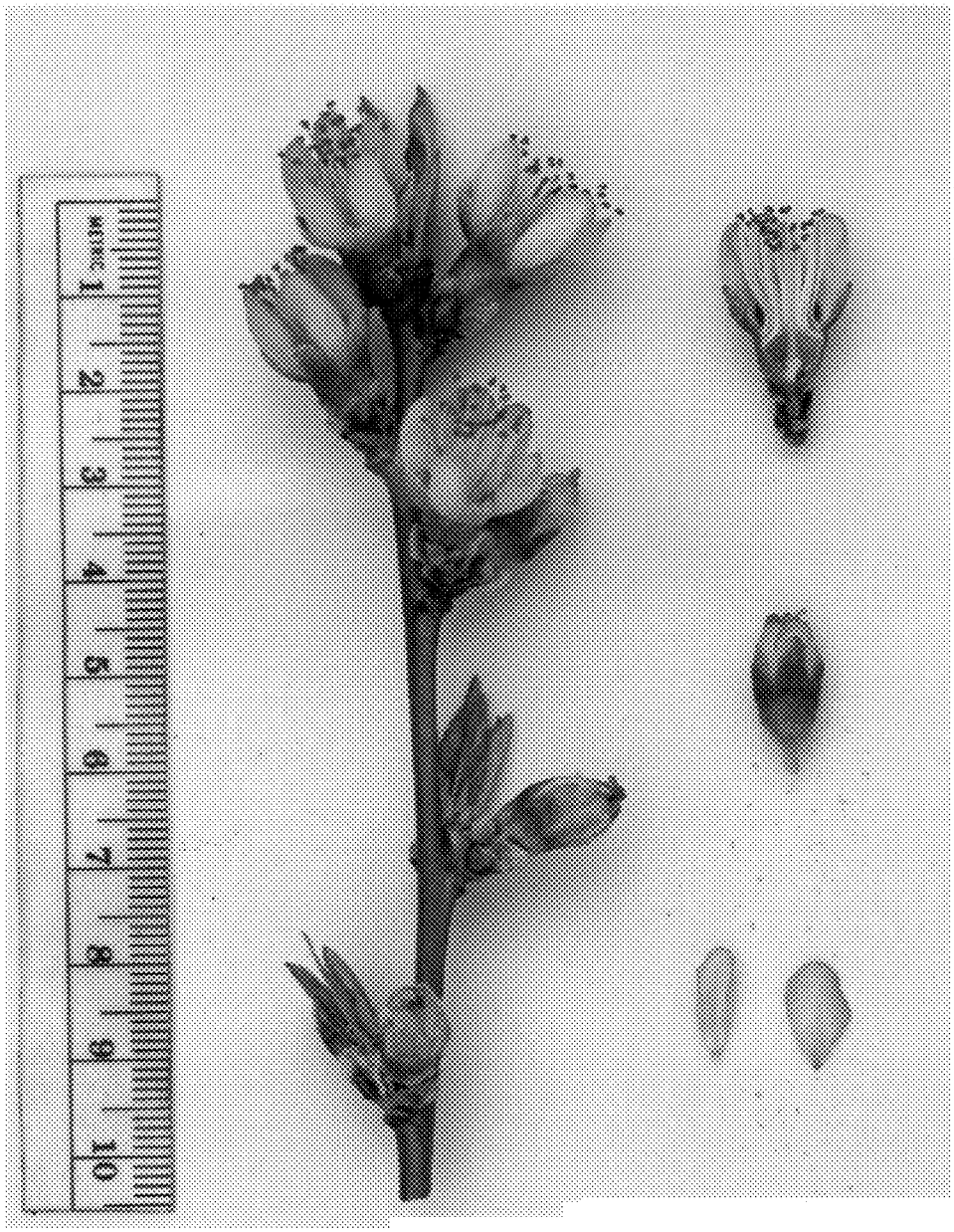
FIG. 3 is a color photograph of a characteristic twig that illustrates the typical flower buds and large, showy flowers of 'NJ355' observed on a tree that was six years of age on Apr. 21, 2004.
Figure 4:
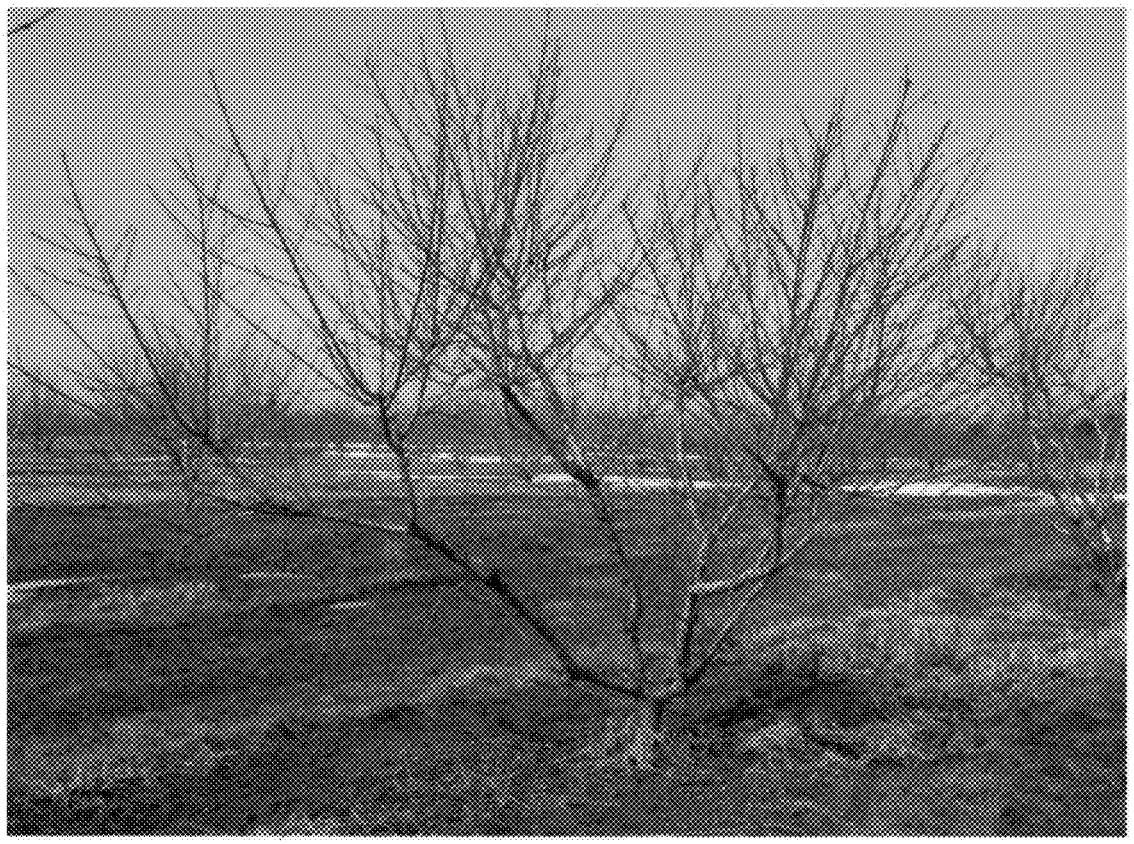
FIG. 4 is a color photograph of a tree of 'NJ355' in late winter, prior to pruning, that illustrates the spreading growth habit of a tree at the fruit research center in Cream Ridge, N.J. on Feb. 17, 2011.
Figure 5:
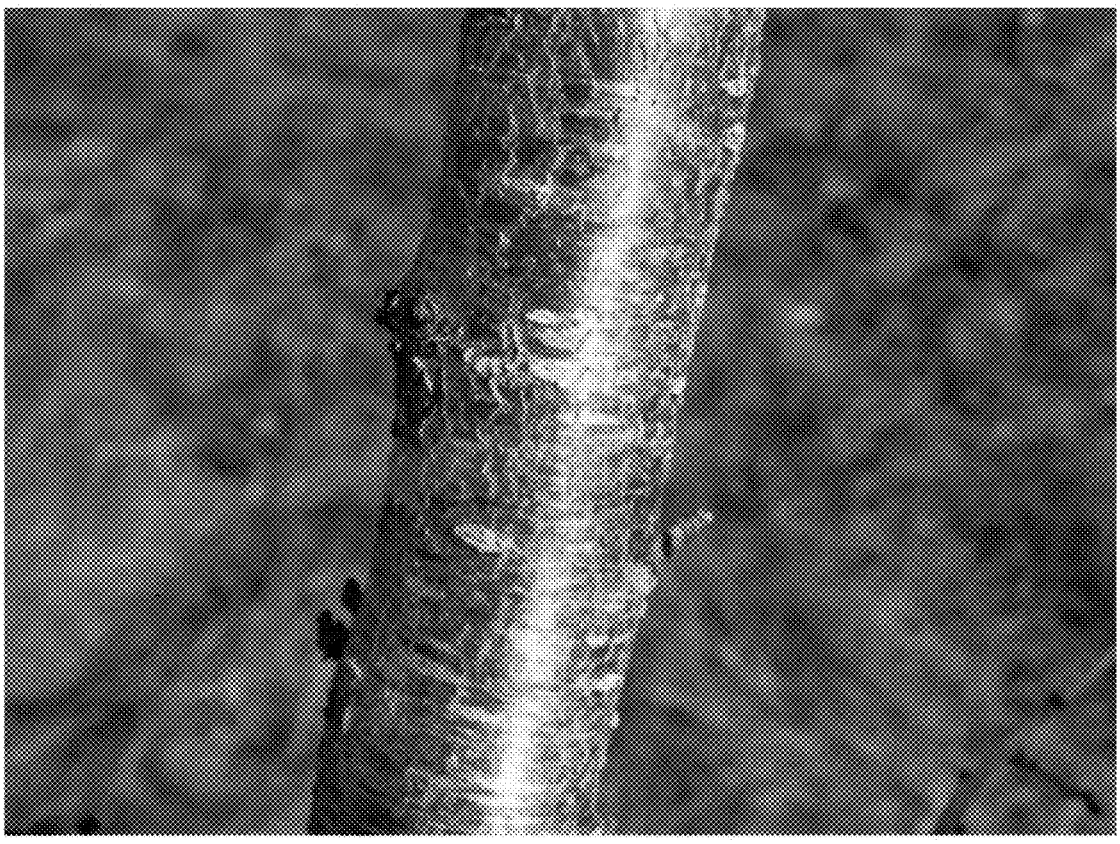
FIG. 5 is a color photograph taken on Feb. 17, 2011 of immature bark of 'NJ355' that illustrates color and the comparatively low density of lenticels that tend to be clustered in small groups on the immature bark.
Figure 6:
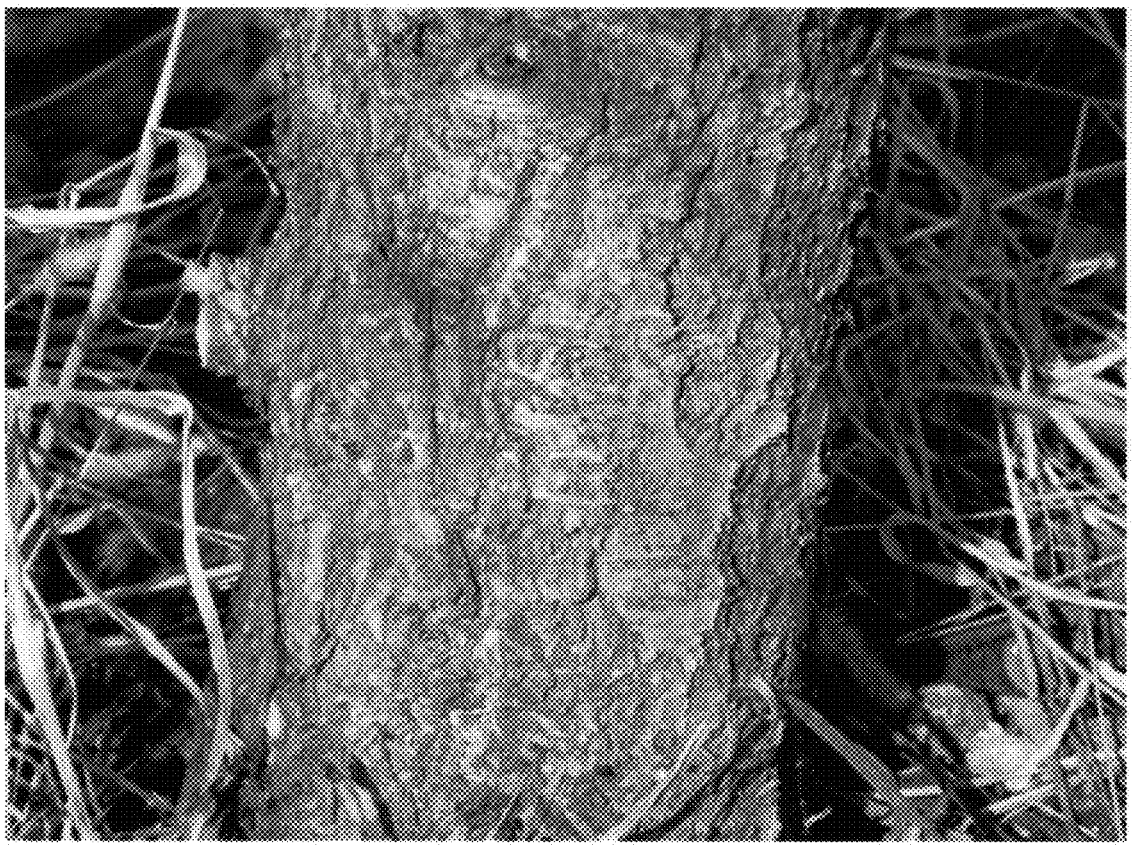
FIG. 6 is a color photograph taken on Feb. 17, 2011 of mature bark of 'NJ355' that illustrates the comparatively rough texture of the mature bark.

The colors and illustration of this type may vary with lighting and other conditions and, therefore, color characteristics of this new variety should be determined with reference to the observations described herein, rather than from these illustrations alone.

DETAILED BOTANICAL DESCRIPTION

The following detailed description of the 'NJ355' variety is based on observations of an asexually reproduced tree. The observed tree was six years of age and growing on 'Lovell' seedling rootstock (unpatented) at the fruit research center in Cream Ridge, N.J.

Scientific name: *Prunus persica* L.

Parentage:

*Seed parent*.—J19-19-862144.

*Pollen parent*.—Unknown.

Tree:

*Vigor*.—Moderate.

*Plant hardiness zone*.—Growth of plants has only been observed in zone 6b.

*Dormant flower bud cold tolerance*.—At least to −20° C.

*Overall shape*.—Spreading.

*Height*.—Slightly above average as compared to other peach cultivars. For example, measurement of a typical grafted tree on 'Lovell' seedling rootstock (unpatented) at six years after planting shows an average height of 3.4 meters when grown in Cream Ridge, N.J.

*Width*.—Slightly above average as compared to other peach cultivars. For example, measurement of a typical grafted tree on 'Lovell' seedling rootstock (unpatented) at six years after planting shows an average width of 5.2 meters when grown in Cream Ridge, N.J.

*Caliper*.—Six year old tree is 43 cm in circumference measured at 20 cm from the ground.

Trunk and branches:

*Trunk bark texture*.—Rough as compared to other peaches of a similar age.

*Trunk bark color*.—Greyed-white (between RHS 156A and RHS 156B).

*Primary branches*.—Branches that are approximately 18 cm in circumference are greyed-orange (RHS 176B) in color, overlaid with greyed-green (RHS 198D). Branch angles range from 45 to 53 degrees, averaging about 49 degrees. Lenticels: Low density, approximately 0.5 per square cm; lanceolate in shape; typical examples of which measured 5 mm in length and 1.2 mm in width; greyed-orange (RHS 174D) in color and bordered with greyed-brown (RHS 199D). Branch pubescence: None. New growth bark: Greyed-red (RHS 184A) in sun; color greyed-yellow (RHS 152D) in shade.

*Internodes*.—Length averaging 21 mm on a one-year shoot.

Leaves:

*Texture*.—Glabrous.

*Sheen*.—Young leaves semi-glossy with a flat finish on the underside. Adaxial surface of mature leaves are generally smooth, glabrous, slightly glossy. Abaxial surface of mature leaves are nearly smooth, glabrous, with a matte finish.

*Length*.—About 154 mm to 193 mm, averaging about 175 mm including the petiole.

*Width*.—About 34 mm to 48 mm, averaging about 40 mm.

*Petiole*.—Averaging 10.4 mm long and about 1.4 mm in diameter.

*Margin*.—Finely serrate.

*Margin undulation*.—Slight.

*Form*.—Lanceolate.

*Apex*.—Acuminate, curved downward.

*Base*.—Cuneate.

*Venation*.—Pinnate.

*Glands*.—Number: About 3 to 6, averaging about 5.3. Position: Located on the leaf margin and petiole. Size: Length averaging 1.1 mm and width averaging 0.8 mm. Form: Reniform.

*Stipules*.—None observed on mature leaves.

*Leaf color*.—Upper leaf surface: Green (between RHS 137B and RHS 137C). Lower leaf surface: Yellow-green (RHS 147B and RHS 147C). Vein: Yellow-green (RHS 147C).

*Pubescence*.—None.

Flowers:

*Size*.—Large size, typical flower measuring between 34 mm to 37 mm, averaging about 36 mm across.

*Color*.—Dormant bud: Greyed-green (RHS 196A) with flecks of grey (RHS 201A). Pink stage bud: Red-purple (between RHS 63B and RHS 63C). Open flower: Red-purple (RHS 62D to RHS 62A near edge).

*Petals*.—Typically five petals per flower; cupped; margin entire, averaging about 11.0 mm long and 7.5 mm wide.

*Petal apex*.—Obtuse.

*Petal base*.—Cuneate.

*Stamens*.—Number: Variable, typical range 30 and 40, averaging 34.6. Length: Between 10.1 mm to 12.2 mm, averaging 10.8 mm. Filament color: Green-white (RHS 157B). Anther color: Red (RHS 46A).

*Pistil*.—Number: One. Size: Length between 14.5 and 17.0 mm, averaging about 15.7 mm. Pistil color: Yellow-green (RHS 146B). Ovary: Pubescent and ellipsoid in shape.

*Sepals*.—Number: Five. Pubescence: Short and low density. Color: Green (RHS 139D) with a greyed-red (RHS 182B) over color. Shape: Triangular, with a rounded apex. Size: Length averaging 6.1 mm, width averaging 4.1 mm.

*Nectar cup color*.—Greyed-orange (RHS 167B) on young flowers, becoming greyed-yellow (RHS 162A) after anthesis.

*Pollen*.—Abundant; yellow-orange (RHS 11A) in color.

*Fragrance*.—Very slight.

*Bloom season*.—Onset of bloom in 2004 on April 19; full bloom on April 22.

Fruit:

*Size*.—Medium, averaging about 5.8 cm long, 6.2 cm wide parallel to the suture and 6.4 cm wide perpendicular to the suture.

*Typical weight*.—139 g.

*Form*.—Longitudinal section: Nearly round, slightly oblate. Traverse section: Nearly round.

*Suture*.—Shallow, extending from the base to apex.

*Ventral surface*.—Nearly smooth.

*Base*.—Flat.

*Apex*.—Hooked, thick, and fleshy.

*Stem*.—Average length of 5.8 mm and an average diameter of 2.6 mm.

*Skin*.—Thickness: Average. Surface: Glabrous, typically glossy. Tenacity: Average, decreasing as fruit becomes too mature. Astringency: None. Tendency to crack: Low. Color: Mottled red (RHS 46A) and greyed purple (RHS 183B) blush; ground color orange-white (RHS 159C).

*Fruit properties*.—Flesh color: Greyed-white (RHS 158C) becoming greyed-yellow (RHS 160D) near the stone. Flesh adhesion: Clingstone. Juice: Moderate. Texture: Very firm, not melting. Fibers: Not noticeable. Ripens: Between July 11 and July 31 at Cream Ridge, N.J. Flavor: Above average, generally sweet and only slightly acidic. Soluble solids: Between 12.4 and 15.6%, averaging about 14.0%. Aroma: Very slight. Eating quality: Good to very good.

*Keeping quality*.—Excellent. Has held its flavor and firmness for at least 21 days in cold storage at 1° C. to 4° C.

*Shipping quality*.—Excellent. Fruit are very firm at harvest. No bruising or scaring disorders have been observed.

*Usage*.—Dessert.

*Market*.—Local and long distance.

*Productivity*.—Excellent. Trees have produced a crop in 10 out of 10 years and a full crop in nine out of ten years at Cream Ridge, N.J.

Stone:

*Type*.—Clingstone.

*Form*.—Ovoid.

*Base*.—Narrow.

*Apex*.—Medium.

*Surface*.—Pit grooves.

*Ventral suture*.—Medium.

*Dorsal ridge*.—Medium depth with deep lines.

*External color*.—Greyed-orange (between RHS 165C and RHS 165D).

*Internal color when cracked*.—Greyed-yellow (between RHS 161C and RHS 161D).

*Cavity surface color*.—Greyed-orange (RHS 165D).

*Average stone dry weight*.—2.9 g.

*Average stone wall thickness*.—Varies between 3.4 mm along the ventral suture and 6.3 mm at the base.

*Size*.—Averages about 26.7 mm long, 21.9 mm wide parallel to the dorsal ridge, and 16.0 mm wide perpendicular to the dorsal ridge.

*Tendency to split*.—Low for the ripening season.

*Kernel*.—Form: Highly variable; forms only rudimentary seed. Skin color: Highly variable, greyed-orange (between RHS 165A to RHS 165B). Vein color: Variable, greyed-orange (between RHS 165A and RHS 165C). Viability: No. Size: Highly variable; forms only rudimentary seed averaging about 0.1 g.

Plant/fruit disease and pest resistance/susceptibility: No atypical resistances/susceptibilities have been noted under normal cultural practices.

We claim:

1. A new and distinct variety of peach tree, substantially as herein shown and described.

* * * * *